United States Patent
Fallouh et al.

(10) Patent No.: US 10,420,786 B2
(45) Date of Patent: Sep. 24, 2019

(54) COMPOSITIONS FOR USE IN CARDIOPLEGIA COMPRISING ESMOLOL AND ADENOSINE

(71) Applicant: AOP ORPHAN IP AG, Vaduz (LI)

(72) Inventors: Hazem B. Fallouh, London (GB); Jonathan C. Kentish, London (GB); David J. Chambers, London (GB)

(73) Assignee: AOP ORPHAN IP AG, Vaduz (LI)

( * ) Notice: Subject to any disclaimer, the term of this patent is extended or adjusted under 35 U.S.C. 154(b) by 166 days.

(21) Appl. No.: 15/343,358

(22) Filed: Nov. 4, 2016

(65) Prior Publication Data
US 2017/0100423 A1    Apr. 13, 2017

Related U.S. Application Data

(63) Continuation of application No. 13/203,455, filed as application No. PCT/GB2010/000347 on Feb. 26, 2010.

(30) Foreign Application Priority Data

Feb. 26, 2009    (GB) .................................. 0903299.6

(51) Int. Cl.
| | | |
|---|---|---|
| A61K 31/7076 | (2006.01) | |
| A61K 31/24 | (2006.01) | |
| A61K 33/06 | (2006.01) | |
| A61K 9/08 | (2006.01) | |
| A61K 31/216 | (2006.01) | |

(52) U.S. Cl.
CPC ............ *A61K 31/7076* (2013.01); *A61K 9/08* (2013.01); *A61K 31/216* (2013.01); *A61K 31/24* (2013.01); *A61K 33/06* (2013.01)

(58) Field of Classification Search
CPC ... A61K 31/7076; A61K 31/216; A61K 31/24
See application file for complete search history.

(56) References Cited

U.S. PATENT DOCUMENTS

| 7,479,485 B2 | 1/2009 | Belardinelli et al. |
| 2006/0034941 A1 | 2/2006 | Dobson |

FOREIGN PATENT DOCUMENTS

| GB | 2436255 A | 9/2007 |
| WO | 2004/056181 A1 | 7/2004 |
| WO | 2009/1051654 A2 | 8/2009 |

OTHER PUBLICATIONS

"Local Anesthetic" definition by WordNet Search—3.1, also available at http://wordnetweb.princeton.edu/perl/webwn?s=local+anesthetic&sub=Search+WordNet&o2=&o0=1&o8=1&o1=1&o7=&o5=&o9=&o6=&o3=&o4=&h=; last accessed Nov. 3, 2016.
Bessho et al., "Myocardial protection: the efficacy of an ultra-short-acting beta-blocker, esmolol, as a cardioplegic agent", J Thorac Cardiovasc Surg, 122(5):993-1003 (2001).
Chambers, "Mechanisms and alternative methods of achieving cardiac arrest", Ann Thorac Surg, 75(2):S661-6 (2003).
Fallouh et al., "Targeting for cardioplegia: arresting agents and their safety", Curr Opin Pharmacol, 9(2):220-6 (2009).
Ibrahim et al., "A clinical comparative study between crystalloid and blood-based St Thomas' hospital cardioplegic solution", Eur J Cardiothorac Surg, 15(1):75-83 (1999).
Pirk et al., "The effect of the ultrashort beta-blocker esmolol on cardiac function recovery: an experimental study", Eur J Cardiothorac Surg, 15(2):199-203 (1999).
U.S. Department of Health and Human Services, "Guidance for Industry: Container Closure Systems for Packaging Human Drugs and Biologics", (1999). 56 pp.
Bessho et al., "Myocardial protection with oxygenated esmolol cardioplegia during prolonged normothermic ischemia in the rat." The Journal of Thoracic and Cardiovascular Surgery 124(2):340-351 (2002).
Bessho et al., "Experimental study of intermittent crossclamping with fibrillation and myocardial protection: reduced injury from shorter cumulative ischemia or intrinsic protective effect?." The Journal of Thoracic and Cardiovascular Surgery 120(3):528-537 (2000).
Chang et al., "Interactions of esmolol and adenosine in atrioventricular nodal-dependent supraventricular tachycardia: implication for the cellular mechanisms of adenosine." Cardiology 97(3):138-146 (2002).
Dobson "Organ arrest, protection and preservation: natural hibernation to cardiac surgery." Comparative Biochemistry and Physiology Part B: Biochemistry and Molecular Biology 139(3):469-485 (2004).
Dobson et al., "Adenosine and lidocaine: a new concept in nondepolarizing surgical myocardial arrest, protection, and preservation." The Journal of Thoracic and Cardiovascular Surgery 127(3):794-805 (2004).
McCully "Oxygenated multidose delivery of crystalloid esmolol cardioplegia as an alternative to high potassium cardioplegia." The Journal of Thoracic and Cardiovascular Surgery 124(2):219-220 (2002).
Yamaguchi et al., "Lidocaine-magnesium blood cardioplegia was equivalent to potassium blood cardioplegia in left ventricular function of canine heart." Interactive Cardiovascular and Thoracic Surgery 6(2):172-176 (2007).

*Primary Examiner* — Shaojia A Jiang
*Assistant Examiner* — Bahar Craigo
(74) *Attorney, Agent, or Firm* — Nixon Peabody LLP; David S. Resnick; Nicole D. Kling

(57) ABSTRACT

The invention related to a composition for use in cardioplegia, said composition comprising (i) esmolol; and (ii) adenosine, wherein in use the concentration of said esmolol is in the range 0.3-1.5 mM, and wherein in use the concentration of said adenosine is in the range 0.1-1.5 mM. The invention also relates to methods of making and using such compositions.

14 Claims, 3 Drawing Sheets

COMPOSITIONS FOR USE IN CARDIOPLEGIA COMPRISING ESMOLOL AND ADENOSINE

CROSS-REFERENCE TO RELATED APPLICATIONS

This application is a continuation application under 35 U.S.C. § 120 of U.S. application Ser. No. 13/203,455, filed Dec. 6, 2011, which is a 35 U.S.C. § 371 national phase entry application of International Application No. PCT/GB2010/000347 filed Feb. 26, 2010, which designated the U.S., and which claims priority to UK Application No. 0903299.6 filed Feb. 26, 2009, the contents of each of which are incorporated herein by reference in their entireties.

FIELD OF THE INVENTION

The invention is in the field of cardioplegia, in particular in the field of compositions for use in cardioplegia such as cardioplegic solutions.

BACKGROUND TO THE INVENTION

Cardioplegia refers to paralysis of the heart using chemicals. Typically this is effected in order to stop a heart during cardiac surgery. During cardiac surgery, the heart is subjected to an elective period of global ischaemia to provide the surgeon with a blood-free operating field and a still, flaccid heart. To protect the heart during ischaemia, a cardioplegic solution is used for rapid arrest and to help protect the heart from ischaemic injury.

Historically the heart used to be stopped in cardiac surgery by clamping the aorta, inducing ischaemia and cooling the heart down. This was called hypothermic ischaemic arrest. Hypothermic arrest led to an invariably lethal condition called the stone heart in up to one out of ten patients undergoing cardiac surgery.

Subsequently, a method of chemically inducing cardiac arrest was developed after decades of research. This ended the occurrence of the condition "stone heart" and made cardiac surgery a much safer procedure. The chemical arrest (cardioplegia) is induced by perfusing the heart with a cardioplegic solution containing moderately high concentrations of potassium (K) in addition to other electrolytes. One of these solutions, known as St. Thomas' Hospital (STH) cardioplegia, has been used as the predominant crystalloid cardioplegic solution world-wide since. STH is used widely in cardiac surgical centres, and relies on an increased potassium concentration to induce arrest; this has been shown to be reasonably effective and safe. However, potassium induces a 'depolarised' arrest that can be associated with increases in intracellular sodium and calcium concentrations; intracellular overload of these ions can be harmful to the heart.

St. Thomas' Hospital (STH) cardioplegia is relatively safe but it causes a shift in the resting membrane potential to a level that can have detrimental effects, such as increasing the intracellular sodium (Na) and calcium (Ca) concentrations. In order to induce arrest without shifting the resting membrane potential, relatively large amounts of pharmacological agents are usually, but not necessarily, required compared with changing the K concentration of the heart. Na channel and Ca channel blockers in addition to K channel openers are examples of these pharmacological agents. Considerable research has been conducted over the past 25 years where various pharmacological agents at high concentrations have been studied with variable outcomes. However these have not been translated to clinical studies due to the safety concerns, such as the slow washout of the agents from the body, which would lead to prolonged toxic effects.

Despite the remarkable improvement offered by St. Thomas' Hospital (STH) cardioplegia over hypothermic ischaemic arrest, it is well established that STH cardioplegia causes a shift in the resting membrane of the heart from about −85 mV to about −50 mV. This is thought to be detrimental because it causes Na and Ca loading which results in ischaemic contracture and poor recovery of the heart.

Chang et al (2002 Cardiology, volume 97, pages 138 to 146) disclose a study of interactions of esmolol and adenosine in atrioventricular nodal-dependent supraventricular tachycardia. Adenosine is known to operate via the direct effect on activation of the adenosine-sensitive potassium current. However, at the time, less was understood about the indirect effect of adenosine on antagonism of catecholamine-stimulated adenylate cyclase activity. Indeed, there were conflicting reports on this subject in the art at the time of this publication. In order to address this, Chang et al studied the beta-adrenergic blockade to determine whether or not it would potentiate the effects of adenosine. Thus, in the course of this study, low dose esmolol infusion was occasionally practised on a subject, and adenosine infusion was also practised on the same subject. This study was confined to the subject of tachycardia. Esmolol and adenosine were consistently treated as separate and non-overlapping reagents in addressing tachycardia in this study. Indeed, Chang et al conclude that esmolol pre-treatment did not produce any positive synergistic effect on the efficacy of adenosine-induced termination of supraventricular tachycardia. Thus, there is no disclosure towards using a dual esmolol/adenosine treatment. Furthermore, the subject matter of this publication is tachycardia. There is no disclosure in connection with cardioplegia in this document.

Bessho and Chambers (2000 Journal of Thoracic and Cardiovascular Surgery, volume 120, pages 528 to 537) disclose a study of intermittent cross-clamping with fibrillation and myocardial protection. In particular, this study investigated whether injury was reduced principally due to the shorter cumulative ischemic period, or whether there was in fact an intrinsic protective effect. This was a comprehensive study, which compared at least nine different regimes and perfusion protocols. For example, FIG. 1 on page 530 of this document summarises the range of regimes examined. The authors made numerous conclusions from this study, the most important being that equivalent levels of myocardial protection were achieved using either multidose cardioplegia, or using intermittent cross-clamping (with or without fibrillation). These findings allowed the authors to conclude that intrinsic preservation by intermittent cross-clamping with fibrillation did not exacerbate ischemic injury. Nowhere in this document is the use of esmolol disclosed. Nowhere in this document is the use of adenosine disclosed.

Bessho and Chambers (2001 Journal of Thoracic and Cardiovascular Surgery, volume 122, pages 993 to 1003) disclose the efficacy of esmolol as a cardioplegic agent. The authors had noticed that it was a common surgical practice to use intermittent cross-clamping with fibrillation as an alternative to cardioplegia during myocardial re-vascularisation. They were also aware that intermittent cross-clamping with fibrillation offered an intrinsic protection equivalent to the use of cardioplegia. Following on from these observations, the authors investigated whether arrest (rather than fibrillation) during intermittent cross-clamping might be beneficial. They also compared intermittent esmolol cardioplegia with global ischaemia. In the course of the study disclosed, the inventors compared arrest using esmolol only, arrest using the classic St Thomas' Hospital (STH) cardioplegia, and intermittent cross-clamp fibrillation (ICCF). The authors concluded that intermittent arrest with esmolol does not enhance protection of intermittent cross-clamping with fibrillation. However, multiple esmolol infusions during global ischemia did provide improved protection. Further conclusions were drawn from various comparisons between constant flow and constant pressure infusion. However, use of adenosine is not mentioned anywhere in this document. No combination of esmolol and adenosine is disclosed in this publication.

McCully (2002 Journal of Thoracic and Cardiovascular Surgery, volume 124, pages 219 to 220) discusses the use of oxygenated multidose delivery of crystalloid esmolol cardioplegia as an alternative to high potassium cardioplegia. The numerous different approaches taken in the art at that date are reviewed in this editorial. Furthermore, oxygenated multidose crystalloid esmolol cardioplegia is critically assessed for its provision of myocardial protection. It is concluded that esmolol cardioplegia might provide a useful alternative to a traditional high potassium depolarizing cardioplegia. Nowhere in this editorial is the use of adenosine disclosed.

Bessho and Chambers (2002 Journal of Thoracic and Cardiovascular Surgery, volume 124, pages 340 to 351) investigated myocardial protection using oxygenated esmolol cardioplegia during prolonged normothermic ischemia. This publication built on previous work which showed that multidose infusions of high dose esmolol provided excellent myocardial protection under normothermic global ischemia conditions. This publication specifically addressed the importance of oxygenation in achieving optimum protection. A robust comparative study was disclosed which compared the use of the St Thomas' Hospital (STH) cardioplegia together with oxygenated and un-oxygenated esmolol based cardioplegia. This study presented the important finding that oxygenated esmolol cardioplegia could completely protect the heart at certain timescales under normothermic global ischemia. This study clearly demonstrated that deoxygenated esmolol cardioplegia was significantly less protective, and that oxygenation of standard STH solution did not alter its protective efficacy under the conditions used. Related conclusions in the area of comparing constant pressure to constant flow infusion were also disclosed. In summary, this publication teaches the importance of oxygenation when using esmolol cardioplegia in order to obtain optimal myocardial protection. There is no disclosure of the use of adenosine anywhere in this document.

UK patent application number 0711805.2 was published as GB 2 436 255 A on 19 Sep. 2007. This document is concerned with organ preconditioning, arrest, protection, preservation and recovery. This document discloses compositions comprising anaesthetic, adenosine receptor agonist, and anti-adrenergic compounds. This document discloses extremely large numbers of potential individual identities of these generic components. For example, the adenosine receptor agonist is said to be selected from a list of several dozen alternatives. Myriad options are disclosed for the other elements of the composition. Amongst the wide range of different possible alternative ingredients for the compositions discussed, esmolol and adenosine are mentioned. In particular, page 30 lines 20 to 29, page 31 lines 1 to 2, and page 31 lines 14, 15 and 16 each disclose specific possible compositions which include both adenosine and esmolol.

Firstly, it should be noted that this document discloses esmolol and adenosine as minor components of their composition. Furthermore, it is important to note that the concentrations of adenosine used, and particularly the concentrations of esmolol used, are very low. Moreover, it is important to understand the nature of the disclosure made in this document. This document is concerned with the use of anaesthetic such as lidocaine (sometimes referred to as lignocaine) as an arresting agent for induction of cardioplegia. Although the overall disclosure made in this document is at times obscure, for example in trying to reconcile the numerous divergent possible medical uses asserted for the compositions throughout the specification, and for example in trying to reconcile different elements of the disclosure which refer to different numbers of components in the compositions being described, and for example in trying to ascribe different functions to different components from the long lists presented, it is nevertheless clear that the only way in which arrest could be produced using the compositions disclosed is via the action of the anaesthetic component lidocaine. The function of the small amounts of esmolol and/or adenosine present in these compositions is limited to a protective effect. Lidocaine is toxic. Lidocaine has a long half-life in vivo of about 2 hours, and relies on the liver for clearance. The liver function can be compromised in cardiac surgery patients, which prolongs the lidocaine half-life even further. These factors can lead to dangerous build up of toxicity during lidocaine-induced cardioplegia. Anaesthetic such as lidocaine is an essential feature of the compositions disclosed in this document, as indicated in the abstract, the main claim, and throughout the description of the application. There is no disclosure in this document of the use of esmolol or adenosine as cardioplegic agents for the induction of arrest.

The present invention seeks to overcome problems associated with the prior art.

SUMMARY OF THE INVENTION

Prior art arresting agents such as lidocaine are toxic. Application of these agents to a patient at the doses required therefore has undesirable side-effects of toxicity. Moreover, in addition to toxicity at the dose given, there is a build up of the compounds used in the periphery of the patient's body, which can lead to further drawbacks and complications. Esmolol and adenosine have been included in certain compositions in the prior art in combination with an arresting agent. Prior art compositions comprising esmolol and adenosine have used very low levels of those substances, and have been used as protectants only. It is possible to use esmolol only in order to cause arrest, but only at problematically high concentrations. This has made the use of esmolol only as an arrestant problematic in the prior art.

The present inventors have surprisingly found a synergistic relationship between adenosine and esmolol in cardioplegia. Specifically, the inventors have found that within certain specific concentration ranges of these two substances, the inclusion of adenosine lowers the effective concentration of esmolol needed to induce arrest. In other words, inclusion of adenosine at specific concentrations in a cardioplegic solution of the invention renders it possible to safely use esmolol as an arrestant in the same composition. Following on from these initial discoveries, the inventors have now defined specific windows or ranges of concentrations of these two active ingredients which, when used in combination, provide excellent cardioplegic effects together with minimised damage/enhanced functional recovery after cardioplegia.

Thus in one aspect the invention provides a composition for use in cardioplegia, said composition comprising
(i) esmolol; and
(ii) adenosine,
wherein in use the concentration of said esmolol is in the range 0.3-1.5 mM, and
wherein in use the concentration of said adenosine is in the range 0.1-1.5 mM.

This is a new combination of active ingredients, which combination of concentrations has the surprising effect of permitting esmolol to act as an effective arrestant. This effect is not seen with prior art compositions comprising esmolol, because such prior art compositions have been at concentrations too low to exhibit this effect, and also because prior art compositions have been based on use of non-esmolol arrestants. Thus, prior art compositions have featured only de minimis and sub-arresting levels of esmolol present as protectant.

This has the advantage of avoiding use of toxic arrestants such as lidocaine.

For use in cardioplegia is intended to imply that the composition is capable of effective arrest of a heart i.e. capable of actually being used to induce cardioplegia if administered to a subject. In case any further guidance is needed, there are numerous experimental systems in use in the art for testing this property. In case any further guidance is required, exemplary test systems are as disclosed in the examples section. Suitably the cardioplegia is human cardioplegia i.e. for use implies suitably implies for use in humans.

In another aspect, the invention relates to a composition as described above wherein the concentrations of esmolol and adenosine correspond to a single point in the enclosed area on the graph of FIG. 4. This graph is explained in more detail in the examples section. This has the advantage of defining particularly advantageous pairs of adenosine and esmolol concentrations.

In another aspect, the invention relates to a composition as described above wherein the concentrations of esmolol and adenosine correspond to a single point in the hatched area on the graph of FIG. 4. This hatched area described particularly advantageous pairs of esmolol and adenosine concentrations.

In another aspect, the invention relates to a composition as described above wherein the product of the concentration of esmolol and of adenosine is at least 0.15, more suitably the product of the concentration of esmolol and of adenosine is at least 0.3, more suitably the product of the concentration of esmolol and of adenosine is at least 0.45. The product of the concentration of esmolol and of adenosine is a dimensionless coefficient i.e. it has no units. This may be calculated by simply multiplying together the concentration of adenosine and the concentration of esmolol, provided only that the two concentrations are expressed in the same units (i.e. both mM or both uM or both M etc.). The resulting value is helpful in relating the two concentrations according to embodiments of the invention. This is particularly the case because of the partial reciprocal nature of the interrelationship between the two values; in other words (within certain limits as set out herein) the greater the concentration of adenosine the lower the concentration of esmolol forms an effective arrestant; for lower concentrations of adenosine a greater amount of esmolol is needed for arrest. Thus, preferred embodiments of the invention may be described with reference to the product of the two concentrations. An advantage of these embodiments is that the total amounts of active ingredients used may be limited by choosing effective concentrations having this property.

Suitably said composition comprises a crystalloid or blood preparation. A blood-based solution is most suitably used as this is used most frequently in the clinical setting.

Suitably said composition comprises 0.6 mM esmolol and 0.25 mM adenosine.

Suitably said esmolol and adenosine are dissolved in a solvent consisting essentially of a physiological solution. Suitably said esmolol and adenosine are dissolved in a solvent consisting essentially of Ringer solution.

In another aspect, the invention relates to use of a composition as described above in the induction of cardioplegia.

In another aspect, the invention relates to a method of inducing cardioplegia comprising administering to a subject a composition as described above.

In another aspect, the invention relates to a composition for use in manufacture of a cardioplegic solution, said composition comprising
(i) esmolol; and
(ii) adenosine,
wherein in use the concentration of said esmolol in the cardioplegic solution is in the range 0.3-1.5 mM, and wherein in use the concentration of said adenosine in the cardioplegic solution is in the range 0.1-1.5 mM; wherein the amounts of esmolol and adenosine present in said composition are at least two times these amounts. Suitably the amounts of esmolol and adenosine present in said composition are at least five times these amounts. Suitably the amounts of esmolol and adenosine present in said composition are at least ten times these amounts. Suitably the amounts of esmolol and adenosine present in said composition are at least twenty times these amounts, or even more, such as one hundred times these amounts. These concentrated compositions find application as stock solutions from which the cardioplegic solution for use may be conveniently diluted or formulated before administration to a subject.

In another aspect, the invention relates to a method for making a cardioplegic solution comprising diluting a composition as described above to produce a solution having a final concentration of esmolol in the range 0.3-1.5 mM, and having a final concentration of adenosine in the range 0.1-1.5 mM.

In another aspect, the invention relates to a method of formulating a cardioplegic solution comprising diluting a composition as described above to a final concentration of 0.6 mM esmolol and 0.25 mM adenosine.

In another aspect, the invention relates to use of a composition as described above in the manufacture of a medicament for inducing cardioplegia.

In another aspect, the invention relates to an ampoule comprising
(i) 25 mM adenosine
(ii) 60 mM esmolol
in aqueous solution.

In another aspect, the invention relates to an ampoule comprising
(i) 75 mM adenosine
(ii) 180 mM esmolol
in aqueous solution.

An ampoule comprising
(i) 67 mg adenosine
(ii) 199 mg esmolol
in 10 ml aqueous solution. This is one example of a composition for manufacture of a cardioplegic solution; suitably the contents of said ampoule are dispersed in 990 mls the final cardioplegic diluent base, making a total of one liter of cardioplegic solution.

An ampoule may be a traditional ampoule, or may be a phial, a glass container, a packet such as a blood bag or any other suitable vessel for the storage or handling of a composition such as a stock solution for manufacture of a cardioplegic solution. These embodiments find application in transport, handling and sale of items and compositions for use in the manufacture of crystalloid or blood based cardioplegic solutions.

To make a blood cardioplegic solution, a stock cardioplegic solution (such as a crystalloid stock cardioplegic solution) is typically diluted with patient blood in a proportion decided on the surgeon's preference, however it should be noted that the final concentration is the same for human blood/crystalloid applications of the invention as explained below.

Suitably a cardioplegic solution according to the present invention is made by mixing the contents of an ampoule of the invention with a suitable diluent such as a crystalloid or blood based solution.

In another embodiment the invention relates to containers comprising a dry mixture of the corresponding masses of adenosine and esmolol as described above.

Suitably the composition is in the form of an aqueous solution.

In some embodiments the invention relates to a pharmaceutical kit or pack comprising at least two containers, one such container comprising esmolol and one such container comprising adenosine. Suitably such a kit or pack comprises an amount of esmolol and adenosine corresponding to a pair of concentration values in use as a cardioplegic solution as described above, for example when diluted or dissolved to one liter.

DETAILED DESCRIPTION OF THE INVENTION

Dobson (patent publication GB2436255A) discloses various compositions based around the use of lidocaine as an arrestant. In a number of those compositions, very small quantities of esmolol and small quantities of adenosine were included as protectants. It is important to note that the concentrations of esmolol used in GB2436255A are very low, and at such low concentrations esmolol functions only as a beta-blocker. The present invention discloses specific ranges of concentrations of esmolol and adenosine for use in combination as arrestants. The present invention specifically excludes the use of lidocaine in compositions of the invention. Thus, the invention suitably omits lidocaine. Compositions of the invention suitably do not comprise lidocaine. Suitably compositions comprising arresting amounts of lidocaine are specifically disclaimed from the invention.

Thus, a combination of three agents (Na channel blocker; K channel opener; β-blocker) is used to induce arrest and protect the heart in the Dobson publication. The Na channel blocker Lidocaine is used in high concentration to induce arrest despite the problematic toxicity of this agent. Esmolol, has been considered as an example of a β-blocker for myocardial protection, but at low concentrations not sufficient to induce or contribute to cardiac arrest.

Due to the specific concentrations of adenosine used in the Dobson patent as protectants, there is a an overlap of some points in connection with the concentration ranges of adenosine taught by the present invention. However, all compositions of the invention specifically require the presence of certain concentrations of esmolol in combination with adenosine. Thus, the compositions of the invention do not overlap with the compositions disclosed in the Dobson patent for at least this reason. The compositions of the invention are further distinguished by an absence of lidocaine. Furthermore, the compositions of the invention are distinguished by the combination of adenosine with esmolol as arrestant. Specifically, the compositions of the invention are distinguished from Dobson by an entirely non-overlapping range of concentrations of esmolol which are specifically required in the compositions of the present invention and which do not overlap at all with any of the concentrations disclosed in the Dobson patent. Moreover, a majority of compositions of the invention are also distinguished from the Dobson patent by virtue of requiring a different concentration of adenosine than those specific values disclosed in the Dobson patent. Thus, for all of these reasons, the claims of the present invention are distinguished over the disclosures of GB2436255A.

In addition to these structural differences, it is important to note that the present invention is concerned with the new and surprising use of esmolol as arrestant. This advantageous technical effect is achieved through combination with adenosine in the compositions of the invention. This combination, specifically when using the concentration ranges given which are an important aspect of the invention, advantageously avoids the use of toxic compounds such as lidocaine. This surprising benefit could not have been predicted from the prior art. This is particularly true since the prior art combinations comprising adenosine clearly and unequivocally relied on toxic compounds such as lidocaine for induction of arrest. Thus, it is a further benefit of the invention that the composition avoids the use of toxic arrestants.

Thus it can be appreciated that the inventors have devised a novel cardioplegic solution that induces arrest via a 'polarised' mechanism, which advantageously prevents ionic imbalance during the ischaemia and has other advantages over STH. The solution of the invention uses a combination of esmolol (an ultra-short-acting b-blocker, which has sodium channel and calcium channel blocking properties) and adenosine (which has potassium channel opening properties).

One advantage of this solution is that the components have relatively short-acting effects, and thus toxic effects of high concentrations are minimised. This has considerable advantages for current cardiac surgery patients, who are older, sicker and have increased morbidity. In particular, the effects of surgery and cardiopulmonary bypass can compromise the function of the liver and kidney; high concentrations of prior art drugs used to arrest the heart may remain in the circulation for extended periods leading to build-up of toxic effects. The components of the solution of the invention do not rely on the liver and kidney for metabolism, and so provide a considerable safety benefit.

DEFINITIONS

The term 'comprises' (comprise, comprising) should be understood to have its normal meaning in the art, i.e. that the stated feature or group of features is included, but that the term does not exclude any other stated feature or group of features from also being present.

Cardiac Surgery and Myocardial Protection

Operating on a beating heart was once standard practice for heart wounds and valve stenosis. However, due to the technical difficulty of operating on a beating heart in a very bloody surgical field and in order to perform more complicated surgery, it was essential to arrest the heart and stop the blood flow through it. This meant dealing with the implication of abolishing the cardiac output for the length of the procedure which would cause irreversible brain injury if it lasted for more than 2-3 minutes in normothermia. This period was extended to 10 minutes by using hypothermia which was long enough to perform the first open heart surgery. The development of cardiopulmonary bypass allowed surgeons to arrest the heart for longer times without major effect on the brain. From then on, it was recognised that inducing arrest and cessation of blood flow to the myocardium for longer periods than a few minutes in order to perform complicated surgery would expose the heart to ischaemic damage. Hypothermia was still the most commonly used method to protect the heart against ischaemia during cardiopulmonary bypass, though without any specific method to arrest the heart except for ischaemia-induced arrest.

The next advance was the concept of chemical reversible cardiac arrest using a high potassium solution. This was the first concept of chemical myocardial protection. The potassium citrate solution used was shown to have detrimental effects on the myocardium leading to myocardial necrosis and increased risk of mortality and, consequently, the use of potassium-based cardioplegia became unpopular. Alternative methods of myocardial protection were described, such as intermittent cross-clamp fibrillation and coronary occlusion. However, the use of cardioplegia was maintained in Germany with the development of the Bretschneider solution which was Na-poor and Ca-free. It was used clinically with success, becoming one of the first solutions to be used routinely in clinical practice.

The detrimental effects of the potassium-citrate based solution were found to result, and to derive from the increased osmolality from the high citrate concentration rather than the high potassium levels. These results revived the concept of cardioplegia in general and hyperkalaemia in particular. Soon after, a formulation with moderately high potassium was developed at St. Thomas' Hospital. This became known as the St. Thomas' Hospital cardioplegia solution No. 1. The success of this solution in protecting the myocardium against global ischaemia and reperfusion injury, identified as the "stone heart phenomenon", made it very widely used. Subsequently, the original formula of the St. Thomas' Hospital No. 1 solution was slightly modified creating the St. Thomas' No. 2 solution. This was registered with the Federal Drug Authorisation (FDA) in the USA and rapidly, became by far the most widely used cardioplegic solution worldwide and it remains the gold standard cardioplegic solution.

The present invention provides improved cardioplegic solutions.

Concentration Ranges

For human use in cardioplegic preparations, suitably esmolol is present at 0.3 millimolar to 1.5 millimolar. 0.3 millimolar is a suitable end point which represents the first reliably useful arresting concentration of esmolol. Less than 0.3 millimolar may be ineffective in consistently producing arrest. 1.5 millimolar esmolol is a suitable upper-end point, since concentrations greater than 1.5 millimolar can be difficult to wash out of the system, or more accurately heart function after concentrations higher than 1.5 millimolar esmolol are removed is less good than function after 1.5 millimolar or lower concentrations are removed.

Suitably, for human use adenosine is present in cardioplegic preparations according to the invention in the range 0.1 to 1.5 millimolar. 0.1 millimolar is a suitable end point for this range since lower concentrations of adenosine are ineffective or less effective in reducing the amount of esmolol needed for arrest. Thus, 0.1 millimolar or higher concentration of adenosine is a useful reliable concentration for effective reduction of the amount of esmolol needed for arrest. 1.5 millimolar adenosine is a suitable upper-end point for adenosine concentration, since use of a greater concentrations of adenosine than 1 millimolar can lead to impaired recovery.

More suitably concentration ranges may be as in the following table:

|  | Upper limit | Lower limit |
| --- | --- | --- |
| [Esmolol] (mM) | 1.5 | 0.3 |
| [Adenosine] (mM) | 1.5 | 0.1 |

Suitably, for human use in cardioplegic preparations adenosine and esmolol are present in the range of concentrations derivable from the enclosed area of the graph in FIG. 4, more suitably from the hatched area of the graph in FIG. 4.

For cardioplegic preparations of the invention, 0.3 millimolar (mM) esmolol is a particularly suitable concentration. This concentration provides good arrest, but also has the benefit of a good wash out from the system, and good functional recovery for the heart once washed out. Clearly, as explained herein, lower concentrations of esmolol are most suitably paired with higher concentrations of adenosine according to the ranges of concentrations set out for cardioplegic preparations of the invention.

Most suitably a cardioplegic preparation according to the invention comprises 0.25 mM adenosine and 0.6 mM esmolol.

Flow Rates and Variable Concentration

It should be clearly understood that the cardioplegic solutions of the invention are suitably for human use and thus the cardioplegic solutions of the invention are discussed in terms of their final concentrations (i.e. their concentrations in use when administered to a human subject). For human hearts, viscosity effects are not likely to alter the final concentrations of substances used in the cardioplegic solutions of the invention so that the concentrations discussed herein apply equally to cardioplegic solutions of the invention for use with human subjects, whether those are colloid, crystalloid, blood based, or any intermediate/mixed base preparation.

A crystalloid preparation is a water-based solution. This offers the advantage of high flow rate and high volume throughput. For example, flow rates of 12 to 14 milliliters per minute can be observed in rat heart. Thus, with such high flow rates, correspondingly lower concentrations of active ingredients can be used, such as 1 millimolar esmolol.

Blood cardioplegia involves use of preparations with higher viscosity. Typical flow rates of 3 to 4 milliliters per minute are achieved in rat heart. Thus, faced with a flow rate approximately one third of that of a crystalloid preparation, a concentration of active ingredient is typically multiplied by 3 in order to provide the same notional rate of delivery.

In this example, if an esmolol concentration of 1 millimolar is used with a crystalloid preparation flowing at 12 to 14 milliliters per minute, then the equivalent concentration for blood-based cardioplegia with a flow rate of approximately 3 to 4 milliliters per minute is 3 millimolor esmolol. This method of converting values given for crystalloid preparations to values suitable for use in blood-based preparations can be applied throughout the invention unless the context indicates otherwise, but it must be borne in mind that values given herein are typically final concentrations (i.e. concentrations in use) for humans and therefore apply equally to either type of preparation. These flow rate variations are intended primarily to assist in understanding the model systems in which the invention is demonstrated.

Thus it can be appreciated that crystalloid compositions have higher flow rates in perfusion in the animal model systems used. Therefore crystalloid compositions can 'deliver' the active ingredients to the heart at a faster rate in those settings. For this reason, crystalloid compositions used in the model systems of small animal hearts can comprise lower concentrations of active ingredients esmolol and adenosine yet still deliver the same effective dose for cardioplegia. Of course the distinction between crystalloid and blood based solutions might be less meaningful if hybrid solutions for example dilute blood based solutions which comprise for example 50% blood base and 50% crystalloid base are used. For any such embodiments then the concentrations of active ingredients such as esmolol and adenosine used should be varied in proportion to the proportion of blood in the mixture e.g. for a mixture that is 50:50 blood to crystalloid then the concentrations should be 50:50 blood to crystalloid i.e. the mean of the concentration for blood and for crystalloid, and so on for other proportions. Alternatively the concentration of active ingredients used may be varied in proportion to the viscosity of the resulting mixture. If the viscosity of the mixture is half way between blood and crystalloid then the concentrations used should be half way between blood and crystalloid (i.e. the mean of the two concentrations), and so on for other proportions. Most suitably the concentration of active ingredients for small animal hearts should be varied according to the flow rate achieved with the different preparations. For example, if a flow rate of 3 ml/min is achieved with a blood based preparation and a flow rate of 6 ml/min is achieved with a mixed preparation then the concentrations for the mixed preparation can be half that (i.e. 3/6) of the concentrations used with the preparation having a flow rate of only 3 ml/min. The underlying principle is to aim for a consistent 'delivered dose' as defined by the ranges and values given herein for different compositions. Notwithstanding this discussion, which is provided to aid understanding of flow rates and the effects in model systems discussed below, it is important to note that embodiments of the invention provide for the same concentrations of active ingredients for human cardioplegic solutions regardless of whether they are crystalloid or blood based cardioplegic solutions.

For ease of understanding, some of the broadest ranges given herein encompass crystalloid and/or blood based compositions for human use; for the avoidance of doubt the graph of FIG. 4 or other specific guidance presented herein should advantageously be consulted to discern the most suitable concentrations for a given application e.g. crystalloid or blood based (or mixed embodiment if applicable).

Esmolol

Esmolol (ASL-8052) (Esmolol Hydrochloride) is a phenoxypropranolamine. Esmolol is a beta1-selective (cardioselective) adrenergic receptor blocking agent with a very short duration of action (half-life in blood is approximately 9 minutes). The molecule has an ester link in the para-position of the phenyl ring that is responsible for the esmolol cardioselectivity and ultra-short duration of action of the drug. It is registered in the UK for the treatment of supraventricular tachycardia, post-operative hypertension and tachycardia syndrome (BNF).

Esmolol Hydrochloride is: (±)-Methyl p-[2-hydroxy-3-(isopropylamino) propoxy] hydrocinnamate hydrochloride and has the following structure:

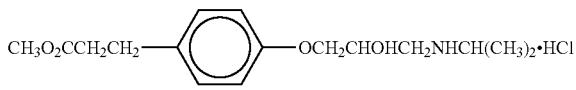

Esmolol Hydrochloride has the empirical formula C16H26NO4Cl and a molecular weight of 331.8. It has one asymmetric centre and exists as an enantiomeric pair.

Esmolol Hydrochloride is a white to off-white crystalline powder. It is a relatively hydrophilic compound which is very soluble in water and freely soluble in alcohol. Its partition coefficient (octanol/water) at pH 7.0 is 0.42 compared to 17.0 for propranolol.

Esmolol may be dissolved in water. Esmolol is suitably provided as stock (750 mmol/L) in aqueous solution. The typical esmolol stock/buffer contents from commercially available sources comprise: sodium acetate trihydrate, acetic acid, propelen glycol, ethanol, HCl for pH adjustment.

Esmolol is widely available. Esmolol may suitably be obtained from Orpha-Devel Handels and Vertriebs GmHB, Austria. This supplier typically provides a stock solution in vials at 750 mmol/L. Alternatively esmolol may be obtained as Brevibloc® from Baxter either as a stock solution or as a more dilute preparation.

Adenosine

Adenosine is a purine nucleoside. It is an endogenous nucleoside occurring in all cells of the body. Adenosine (CAS 58-61-7) has the formula C10H13N5O4 and the systematic name (2R,3R,4S,5R)-2-(6-amino-9H-purin-9-yl)-5-(hydroxymethyl)oxolane-3,4-diol (or 6-amino-9-beta-D-ribofuranosyl-9-H-purine).

Adenosine is a white crystalline powder. It is soluble in water and practically insoluble in alcohol. Solubility increases by warming and lowering the pH of the solution.

Adenosine is suitably provided as powder and dissolved in water.

Adenosine is widely available. Adenosine may suitably be obtained as a powder from Sigma Inc. Attention must be paid to purity of compounds to ensure human grade material is used. A number of suppliers provide clinical grade material, for example Adenoscan™ or Adenocard® (from Astellas Pharma Inc. U.S.) is provided as powder to dilute in water. An Adenoscan™ vial contains a sterile, non-pyrogenic solution of adenosine 3 mg/mL and sodium chloride 9 mg/mL in water for Injection, q.s. The pH of the solution is between 4.5 and 7.5.

Diluents/Cofactors

Suitably the cardioplegic solution comprises 4-20 mM potassium (K+), most suitably 5 mM.

The protective effects can be enhanced by additional components such as magnesium and/or 2,3 butanedione monoxime (BDM).

Magnesium

Magnesium has the advantage of targeting the sarcolemmal L-type calcium channel, as well as increasing the anti-ischaemic protective properties of the solution.

Suitably the cardioplegic solution comprises 1 to 16 mM magnesium (Mg2+); suitably the cardioplegic solution comprises 16 mM Mg2+. This has the advantage of improving protection. Moreover, using certain concentrations of magnesium may slightly decrease the minimal concentrations of esmolol/adenosine needed to achieve arrest. The range of Mg2+ concentrations to achieve this benefit may be between 1-20 mM, suitably 2-16 mM. Exemplary Mg2+ concentrations may include magnesium concentrations 5, 10, or 15 mmol/L Mg2+; most suitably 10 mmol/L Mg2+.

Butane Dione Monoxime (BDM)

BDM has the advantage of targeting the intracellular myofibrils, inhibiting myofilament activation by calcium ions.

Suitably the cardioplegic solution comprises an effective amount of a calcium desensitiser such as 2,3 butane dione monoxime (BDM). This has the advantage of improving protection and/or improving recovery.

Exemplary BDM concentrations may include 5-20 mM BDM, more suitably 5-15 mM BDM. Specific preferred BDM concentrations may include 5, 10, 15 or 20 mmol/L BDM, more suitably 5, 10 or 15 mmol/L BDM.

A further advantage of using magnesium/BDM in the solution of the invention is that use of one or more of these additional component(s) may allow further optimisation of the esmolol and adenosine concentrations in the cardioplegic solution. More specifically, incorporation of these additional component(s) may permit the reduction of the concentrations of esmolol and/or adenosine in the composition. For example, effects of combined optimal magnesium and BDM concentrations established above with changes in esmolol (0.3, 0.4, 0.5, 0.6 mmol/L) and adenosine (0.15, 0.20, 0.25 mmol/L) concentration combinations may be advantageous.

Suitably the cardioplegic solution comprises Hartmann's solution.

Suitably the cardioplegic solution comprises Ringer's solution.

Suitably the cardioplegic solution comprises Krebs-Henseleit Buffer (KHB).

Suitably the crystalloid composition lacks proteins or has reduced or depleted protein content.

Suitably the crystalloid composition mimics the ionic constituents of plasma.

Diluents may be saline, blood, dextrose or any other physiological crystalloid or colloid solution with the physiological electrolytes Na+, K+, Cl, Ca2+, Mg2+, glucose, or other components.

Low Ca2+ and very low Na+ in crystalloid compositions could also enhance the arresting effect of the combination of the invention which may advantageously decrease the minimal concentrations of the combination of esmolol and adenosine. Suitably [Ca2+] of 0.5-2.5 mM and [Na+] of 20-15 mM (more suitably 100-140 mM) may be used to achieve this benefit.

Further Components

The composition of the invention may further comprise one or more other agents which are known to have myocardial protection properties such as Na channel and/or calcium channel blockers, potassium channel openers, calcium desensitisers may be included as an additional component to the composition of the invention. Any such additional components are suitably used to improve the protection against ischaemia. Inducing arrest is accomplished by the esmolol-adenosine combination and further additional components for arrest are typically not used. It is possible that some embodiments might include a very small concentration of Lidocaine e.g. <0.1 mM. This is a non-arresting amount of Lidocaine. Inclusion of such a non-arresting amount of lidocaine would not detract from the invention. Moreover, the prior art inclusion of lidocaine was at significantly higher and arresting concentrations such as no less than 0.6 mM, thus even in embodiments of the invention which included minimal levels of lidocaine remain distinguished from the prior art since the concentrations used are non-overlapping with (e.g.) Dobson publication GB 2 436 255 A. Most suitably lidocaine is omitted or specifically excluded from the compositions of the invention.

Administration

Suitably the subject treated is a human subject.

Suitably administration is to a human.

Suitably dosages/concentrations provided herein are for human applications.

The cardioplegic solutions of the invention are administered according to any suitable technique known in the art. Choice of particular mode of administration is typically made by the skilled operator such as the surgeon.

Typically in a clinical setting for an adult human subject, one liter of cardioplegic solution will be administered. This volume is typically administered regardless of flow rate considerations which have been explained in connection with the model systems used to demonstrate the invention. This initial dose may be followed up with smaller infusions at appropriate intervals to maintain the arrest e.g. 300 mls solution may be administered 20-30 minutes after the main arresting infusion. The volumes are typically not varied according to flow rates—flow rate/viscosity effects are unlikely to apply to large animal hearts such as human hearts. The concentrations of active ingredients given throughout the application are typically final concentrations used independent of flow rate considerations for human applications.

Cardioplegic solutions are normally administered by infusion into the aortic root after application of the cross-clamp, and consequently delivered antegrade into the coronary arteries. It is normal to deliver a 1 liter infusion volume of either crystalloid or blood cardioplegia in this way at an infusion pressure of around 60-80 mmHg over a 2-3 minute period. This could also be applied directly into the coronary arteries. Subsequent infusions might be administered after 20-30 minutes of global ischaemia depending on the presumed duration of the ischaemia to correct the surgical lesion. As an alternative (or in conjunction) retrograde infusion could be used via the coronary sinus through the coronary veins back to the coronary arteries Infusion may be continuous or intermittent. Suitably intermittent infusion is used.

Suitably the cardioplegic solution is not administered (e.g. infused) under normothermic conditions (i.e. 37 degrees Celsius), suitably the cardioplegic solution is administered at 36 degrees Celsius or less. Suitably the cardioplegic solution is administered at from 4 to 32 degrees Celsius ('cold' to 'tepid'). Suitably the cardioplegic solution is administered at 30-32 degrees Celsius (tepid cardioplegia'). Suitably the cardioplegic solution is administered at room temperature such as 22-24 degrees Celsius, suitably 24 degrees Celsius. Temperatures refer to temperature of cardioplegic solution at infusion; clearly the resulting myocardial temperature will vary according to infusion temperature as well as subject body temperature and other factors.

The term 'for use' suitably also embraces an effective temperature for infusion i.e. suitably a composition of the invention for use in human cardioplegia is for use at an effective temperature such as for use at room temperature.

The compositions of the invention are most suitable for patients on cardiopulmonary bypass in cardiac surgery which typically means that the medical staff have full control of patient cardiovascular system and blood pressure (cardiopulmonary bypass), neurological state (general anaesthesia) and respiratory system (artificial mechanical ventilation).

Further Applications and Advantages

In a broad aspect the invention relates to the use of esmolol and adenosine in combination as an arrestant composition such as a cardioplegic composition.

In a further broad aspect the invention relates to the use of adenosine as a potentiator of cardioplegia induced by esmolol.

In a further broad aspect the invention relates to the use of esmolol as an arrestant in the presence of adenosine.

Suitably the invention specifically excludes the use of toxic arrestants such as lidocaine.

It is an advantage of the invention that as much cardioplegic solution as is needed can be freely given to a subject without having to restrict administration according to concerns regarding side effects such as toxicity.

EXAMPLES

Background to the Examples Section

Figure 1:
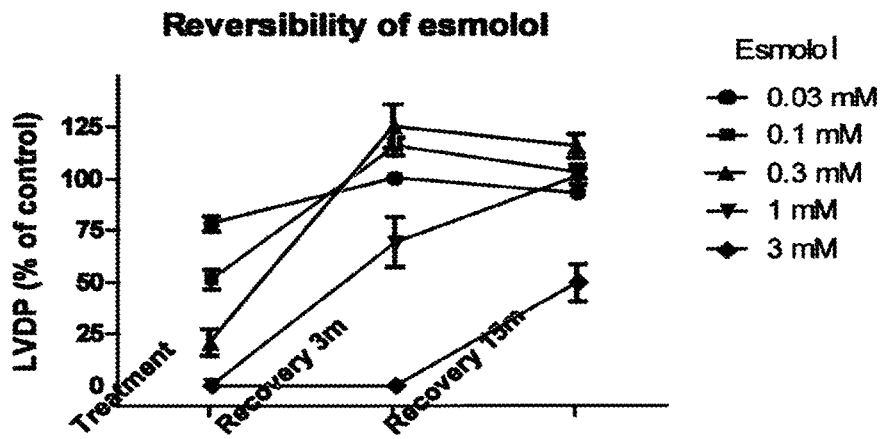
FIG. 1 shows graphs

It is an aim to provide a cardioplegic solution which offers improvement on the current gold standard cardioplegic solution St. Thomas' cardioplegia by creating a solution which arrests the heart without shifting the resting membrane. The following criteria may be considered:

Induce fast cardiac arrest (ideally) in diastole.
Slow the onset of irreversible injury caused by global ischaemia.

These concepts have largely remained limited to animal research for the last 30 years with almost all agents explored have never been tested on human. This is mainly because most of these agents are required in high quantities to induce effective arrest. These quantities can be unsafe to use patients because they accumulate in the body due to the slow metabolism by the liver and the kidney during cardiopulmonary bypass in cardiac surgery. Due to this potential problem in designing potential cardioplegic solutions we propose two additional criteria which the cardioplegic agent should have:

Be reversible quickly once washed out so the heart function is resumed and the cardiopulmonary bypass is weaned off as soon as possible.
Have no or minimal toxic effect on another organ that might linger after cessation of cardiopulmonary bypass. This may be augmented by ensuring that the plasma concentration levels in the peripheral circulation are within the safety margin of each pharmacological agent used in the cardioplegic solution.

This suggests that any pharmacological agent should be used in quantities sufficient to cause arrest and at the same time can be reversed and cleared from the body quickly and reliably in an independent manner from the liver or the kidneys. Examples of such an agent are drug(s) metabolised by the red blood cells (RBCs).

Esmolol is an ultra-short acting β-blocker with half life of 9 minutes due to the fast metabolism by the red cells esterases. Esmolol at low concentrations (0.01-0.1 mmol/L) is used as β-blocker for myocardial protection, hypertension and tachycardia. Due to its myocardial protection properties at these concentrations it has been included as a part of a prior art composition for cardioplegic solution in addition to a Na-channel blocker such as Lidocaine (0.5 mmol/L) along with a K channel opener (Adenosine 0.2 mmol/L)[1]. The arresting effect is founded on the Na channel blocker Lidocaine to induce arrest[2] which is known to be toxic at these concentrations because of the slow clearance from the body as demonstrated by Yamaguchi and colleagues in an in-vivo cardioplegic models[3]. The same limitation applies to almost all other concepts of polarised arrest which have been explored such as Ca channel blockers and potassium channel openers. This has led to the failure of transferring these concepts to clinical practice in the prior art.

Esmolol at concentrations higher than 1 mmol/L can cause cardiac arrest and can be used as a cardioplegic agent through an effect not related its β-blocking action and it is shown to have a comparable outcome to St. Thomas' cardioplegia in in-vitro studies[4,5]. However, esmolol (1.5 mmol/L) has been shown to be slowly reversible with poor recovery in Langendorff perfused rat hearts meanwhile the arrest with esmolol (0.75 mmol/L) was easily reversible[6]. We found that this amount of esmolol was not sufficient to induce effective arrest on its own.

Flow Rates

The invention is exemplified with reference to the accepted model in the art, which uses rat hearts. Although this is the accepted model system and thus regarded as an excellent indicator towards efficacy in humans, it must be borne in mind that rat hearts have a very low coronary artery volume. This is one reason why cardioplegic solutions of differing viscosities (e.g. crystalloid vs blood) may behave slightly differently in the model system used to exemplify the invention. For example, when using a blood-based cardioplegic solution in a rat heart system, concentrations of the active ingredients esmolol and adenosine are usefully increased relative to those used in crystalloid preparations. One reason for this increase is due to the increased viscosity of a blood-based cardioplegic solution. This can lead to a lower flow rate, and thus to a lower notional delivery rate for a given concentration of the active ingredients. For this reason, the concentrations of active ingredients in blood-based cardioplegic solutions are typically increased, which has the advantage of maintaining a desirable delivery rate despite the lower perfusion rate of the more viscous blood-based cardioplegic solution. As a general rule concentrations of esmolol/adenosine used in blood based preparations are approximately three times the concentrations used in crystalloid preparations and vice versa. However, for the reasons explained above, this typically only applies to the small hearts like the rat hearts used in model systems. St. Thomas hospital solution is the gold standard crystalloid and blood at the same final concentrations in human for both. This further supports the notion that the variation of coronary flow is unlikely to be an issue in cardioplegic solutions of the invention (whether blood or crystalloid) in human use.

Example 1

Esmolol and Adenosine Combination

Esmolol and adenosine are rapidly inactivated by the red blood cell esterases and the blood vessel adenosine deaminase respectively. This makes the clearance of these agents fast and independent from the kidneys or the liver, contrary to most other pharmacological agents used as arresting agents in cardioplegia. This makes these two agents an effective combination to be used in a cardioplegic preparation such as a crystalloid preparation at high concentrations to arrest the heart and at the same time they can be cleared from the system rapidly and effectively as when the heart is ready to be started during cardiac surgery e.g. by washing out the drug with blood reperfusion.

We teach the use of Esmolol at concentrations higher than its β-blocking effect (0.01-0.1 mmol/L) to induce arrest and we add adenosine as a synergistic arresting agent in order to use lower amounts of esmolol, yet still surprisingly induce effective arrest. This combination has the benefit of making it easily reversible.

We show this combination to be superior to STH cardioplegia in myocardial protection and post ischaemic recovery. Specific doses and effects are demonstrated in the following examples.

Example 2

Dose Determination

All the following experiments performed in a Langendorff perfused rat heart.

The first study is to determine the reversibility of esmolol at different concentrations after treatment with esmolol for 10 minutes then washout without ischaemia and LVDP was measured 9 minutes after starting the treatment and 3 minutes and 15 minutes after washing out the drug. The following doses were studied 0.03, 0.1, 0.3, 1, 3 mM. (n=5 each group)

1 mM of esmolol was required to induce arrest but 0.3 mM had a better reversibility (LVDP recovery) profile (FIG. 1). It is therefore decided that esmolol concentration between 0.3 and 1 mM offers reasonable arresting effect with good reversibility profile.

Example 3

Combination Dosing

Adenosine was added to esmolol (0.6 mM) at the following concentration: 0.125 mM, 0.25 mM, 1 mM. With normothermic (37° C.) 30 minutes ischaemia.

Esmolol 0.6 mM+ adenosine 0.125 mM arrest time was prolonged cal (70 sec). (Table 1)

Esmolol 0.6 mM+ adenosine 1 mM arrest time was fast but recovery was poor 6 to 40% (Table 2)

It was then decided to study adenosine at 0.25 mM which gives acceptable arresting time (50 seconds) with reasonable recovery

TABLE 1

| Esmolol | Adenosine | Arrest time (Sec) |
|---|---|---|
| 0.6 mM | 0.125 mM | 70 |
| 0.6 mM | 0.25 mM | 53 |
| 0.6 mM | 0.5 mM | 50 |
| 0.6 mM | 1.0 mM | 38 |

TABLE 2

Examples of different concentrations of esmolol + Adenosine (30 minutes ischaemia at 37° C.)

| Esmolol | Adenosine | Baseline | 10 min | 20 min | 30 min | 40 min | 50 min | 60 min | |
|---|---|---|---|---|---|---|---|---|---|
| 0.6 mM | 0.25 mM | 135 | 45 | 55 | 70 | 77 | 75 | 78 | LVDP |
| | | 291 | 276 | 275 | 278 | 279 | 278 | 274 | HR |
| | | 6 | 60 | 57 | 53 | 51 | 51 | 53 | EDP |
| | | | 33.33 | 40.74 | 51.85 | 57.04 | 55.56 | 57.78 | LVDP (% base) |
| 0.6 mM | 1 mM | 156 | 10 | 20 | 37 | 63 | 64 | 62 | LVDP |
| | | 333 | 240 | 260 | 290 | 287 | 274 | 282 | HR |
| | | 4 | 80 | 70 | 63 | 64 | 61 | 65 | EDP |
| | | | 6.41 | 12.82 | 23.72 | 40.38 | 41.03 | 39.74 | LVDP (% base) |
| 0.6 mM | 0.125 mM | 127 | 18 | 21 | 43 | 61 | 65 | 72 | LVDP |
| | | 360 | 262 | 264 | 275 | 252 | 230 | 230 | HR |
| | | 4.5 | 85 | 67 | 57 | 51 | 54 | 52 | EDP |
| | | | 14.17 | 16.54 | 33.86 | 48.03 | 51.18 | 56.69 | LVDP (% base) |
| 0.6 mM | 0.25 mM | 134.8 | 50.5 | 83.75 | 86.18 | 91.19 | 88.93 | 83.31 | LVDP |
| | | 276.6 | 254 | 247.1 | 243.4 | 240.2 | 241.9 | 243.5 | HR |
| | | 4.98 | 57.54 | 44.42 | 43.61 | 45.74 | 47.14 | 48.22 | EDP |
| | | 76.86 | 97.89 | 94.75 | 89.97 | 84.62 | 78.91 | 76.86 | LVDP (% base) |

Example 4

Comparative Study

Figure 2:
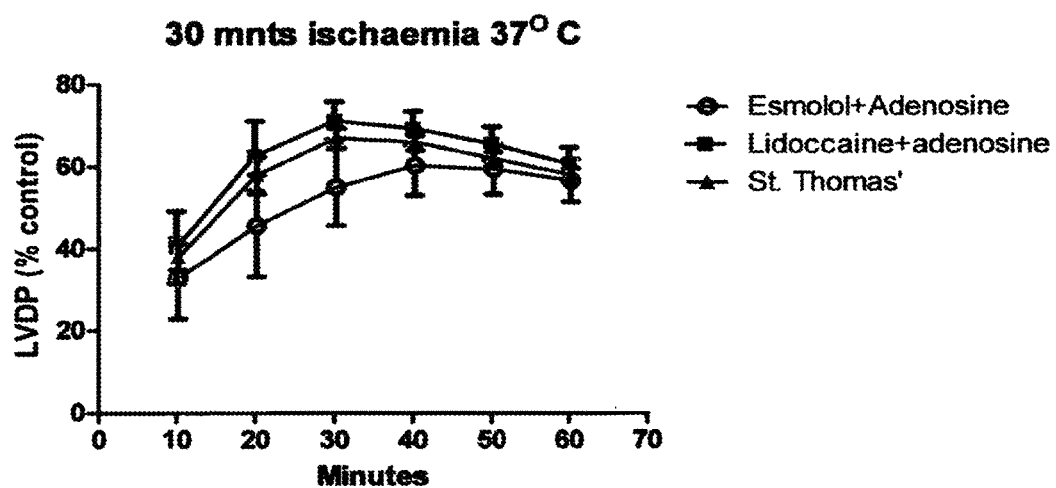
FIG. 2 shows graphs

The (Esmolol 0.6 mM+ adenosine 0.25 mM) was compared with (Lidocaine 0.6+ adenosine 0.25) and STH cardioplegia under normothermia i.e. 37 degrees Celsius (n=5) (FIG. 2). There was no statistically significant difference between the 3 groups but normothermia (37 degrees Celsius) is not the normal practice and the hypothesis was that polarised arrest would offer better protection at lower temperatures which is the practice in cardiac surgery.

We therefore went on to show the combination of esmolol and adenosine to be superior to STH cardioplegia in myocardial protection and post ischaemic recovery at sub-normothermic temperatures. To demonstrate this we randomised 3 groups of male Wistar rat hearts (6 hearts each) perfused in Langendorff mode with 20 minutes stability at 37° C. with Krebs-Henseleit Buffer (KHB), cardioplegic arrest was induced using one of the following 3 solutions: STH, Lidocaine (0.6 mmol/L)+Adenosine (0.25 mmol/L) in KHB and Esmolol (0.6 mmol/L)+Adenosine (0.25 mmol/L) in KHB, then the hearts were exposed to a period of prolonged ischaemia at room temperature (24 degrees Celsius) of 4 hours with multiple infusions (of 3 minutes duration) at 30 minute intervals. After this prolonged ischaemic period the heart was reperfused with This is largely mimicking a prolonged cardiac surgery operation. The results demonstrate superiority of esmolol+adenosine.

Figure 3:
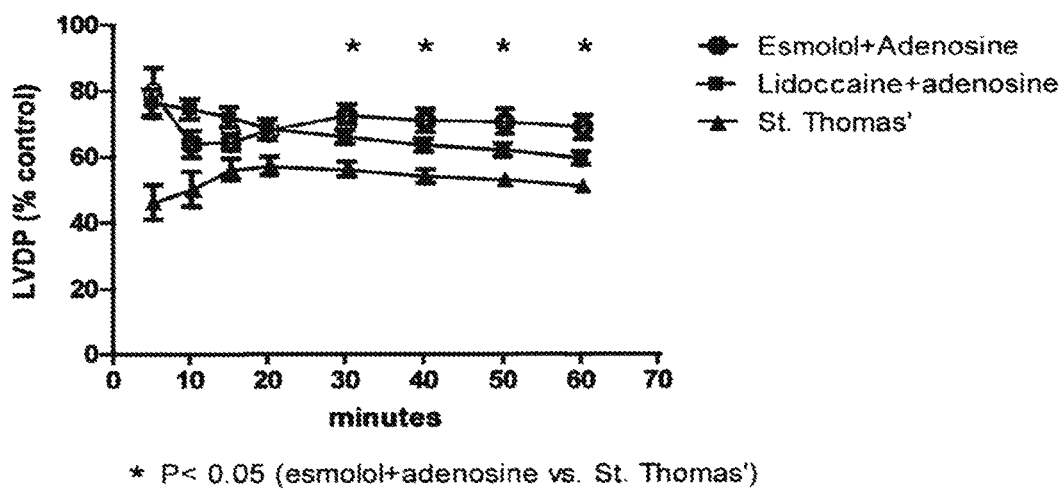
FIG. 3 shows graphs

The experiment was performed in multiple infusion cardioplegia at 30 minutes interval for 4 hours at room temperature (24 degrees Celsius) (n=5) which mimics a very long cardiac operation. Esmolol 0.6 mM+0.25 mM adenosine showed improved recovery profile as demonstrated in FIG. 3.

Thus the effectiveness of the invention is demonstrated with statistically significant data.

REFERENCES TO EXAMPLES 1-4

1. Dobson G P. Organ arrest, protection, and preservation; natural hibernation to cardiac surgery. *Comp Biochem Physiol B Biochem Mol Biol* 2004: 139:469-485.
2. Dobson G P, Jones M W. Adenosine and lidocaine: a new concept in nondepolarizing surgical myocardial arrest, protection, and preservation. *J Thorac Cardiovasc Surg.* 2004; 127(3):794-805.
3. Yamaguchi S, Watanabe G, Tomita S, Tabata S. Lidocaine-magnesium blood cardioplegia was equivalent to potassium blood cardioplegia in left ventricular function of canine heart. *Interact Cardiovasc Thorac Surg* Vol 6; 2007:172-176.
4. Bessho R, Chambers D J. Myocardial protection: the efficacy of an ultra-short-acting beta-blocker, esmolol, as a cardioplegic agent. *J Thorac Cardiovasc Surg.* 2001; 122(5):993-1003.
5. Bessho R, Chambers D J. Myocardial protection with oxygenated esmolol cardioplegia during prolonged normothermic ischemia. *J Thorac Cardiovasc Surg.* 2002; 124:340-351.
6. Pirk J, Kolar F, Ost'adal B, Sedivy J, Stambergova A, Kellovsky P. The effect of the ultrashort beta-blocker esmolol on cardiac function recovery: an experimental study. *Eur J Cardiothorac Surg.* 1999; 15(2): 199-203.

Example 5

Exemplary Pairs of Esmolol/Adenosine Concentrations

It will be appreciated that a key concept underlying the invention is the special relationship between esmolol and adenosine concentrations in the cardioplegic compositions discussed herein. In particular, use of certain levels of adenosine permits effective arrest by correspondingly lower levels of esmolol. Of course there are lower limits as set out herein, below which the effects are less reliable or less advantageous. Similarly there are upper limits which it is advantageous to avoid exceeding for reasons such as impaired recovery if the limits are exceeded. In order to help understand and further define the interrelated amounts of esmolol and adenosine in the compositions of the invention, we present exemplary pairings as defined in the following figures.

Figure 4:
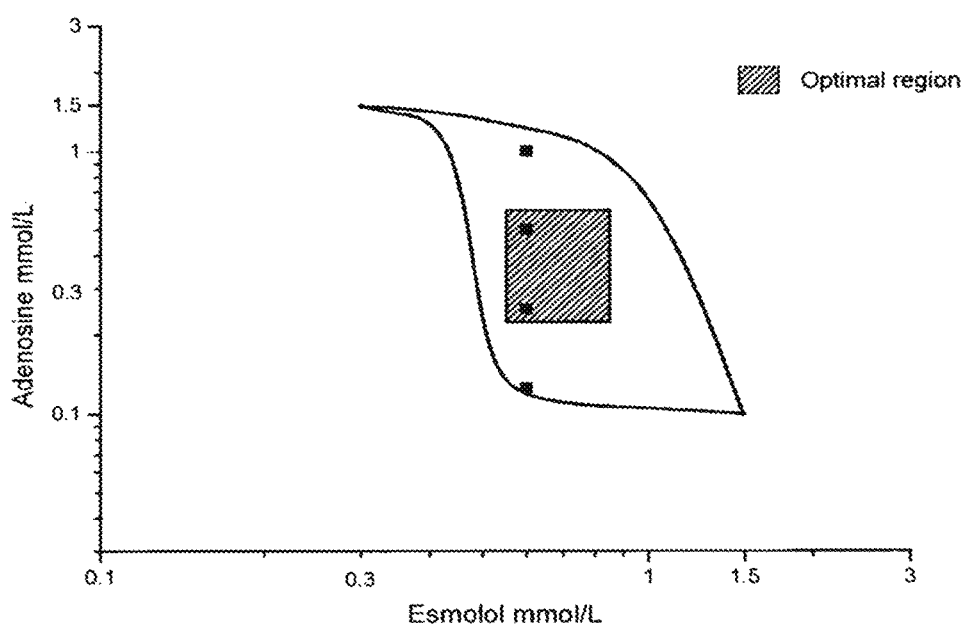
FIG. 4 shows a graph

FIG. 4 shows a graph of adenosine concentration versus esmolol concentration for particularly suitable cardioplegic solutions of the invention.

These graphs define effective pairs of adenosine/esmolol concentrations according to the present invention. The area enclosed by the lines on the graph represents the most suitable active and effective pairs of esmolol/adenosine concentrations. Pairs of concentrations outside the enclosed areas are suitably not used according to the present invention.

It will be apparent that for a given concentration of one of the components, there are alternative concentrations of the other component. For example, referring to FIG. 4, for a concentration of (for example) 1 mM esmolol, a concentration of approx 0.12-0.72 mM adenosine would be suitable. Conversely, for a given concentration of (for example) 1 mM adenosine, a concentration of approx 0.45-0.82 mM esmolol would be suitable. Thus a theroretical line on the graph exists for any given concentration of a first component, and that part of the line within the enclosed area of the graph defines suitable concentrations of the second component which may be used in combination with said given concentration of first component. Clearly it does not matter which of esmolol or adenosine is the first or second component—the graph may be used in the same manner to choose effective concentrations for the second component given any effective concentration of the first component.

Thus it is demonstrated how the graphs may be used to derive ranges of effective concentrations for the two components given a concentration chosen for only one of them.

Equally if there is no particular concentration of one of the components, the graphs may be used to define pairwise combinations by simply selecting a point within the enclosed area and reading off the esmolol and adenosine concentrations from the appropriate axes for that point.

Moreover, the outer reaches of the enclosed areas provide further information on working the invention by defining the possible extremes of the ranges of preferred concentrations for esmolol and adenosine. For example, according to FIG. 4 esmolol concentration may be varied from 0.3 mM to 1.5 mM and adenosine may be varied from 0.1 mM to 1.5 mM.

The shape of the enclosed area also sheds light on the restrictions of the effective doses/concentrations. For example, near the outer limits of the working ranges of adenosine/esmolol according to the present invention, the range of acceptable concentrations for the second component is correspondingly narrower. Thus, referring to FIG. 4, if the concentration of esmolol used is at the lower limit of 0.3 mM, then the amount of adenosine used needs to be correspondingly higher at 1.5 mM whereas for a mid-range value of esmolol concentration such as 0.9 mM, the amount of adenosine used may vary more widely from about 0.125 mM to about 0.9 mM. Thus the graphs may be used to read off more preferred ranges of concentrations for particular pairings or embodiments.

It should be noted that the graph of FIG. 4 is particularly suitable for human cardioplegic preparations of the invention.

With reference to FIG. 4, most preferred pairs of concentrations of esmolol and adenosine for cardioplegic solution embodiments of the present invention are comprised in the hatched section of the graph, which occurs within the enclosed area of the graph. Thus, within the effective pairs of concentrations disclosed by the enclosed area, particularly suitable pairs of concentrations are disclosed by the hatched area; equally it will be apparent that particularly suitable ranges of concentrations of esmolol and adenosine are disclosed by the upper and lower limits of the hatched area in the x- and y-dimensions respectively. Moreover, the four black squares in FIG. 4 represent selected embodiments; the two embodiments represented by the black squares within the hatched area are especially preferred.

Example 6

Optimisation of Cofactor Concentrations

We have demonstrated improved protection during and after ischaemia in isolated rat hearts using compositions of the invention when compared to STH.

In this example we extend these studies and develop the cardioplegic solution by examining whether the protective effects can be enhanced by additional components (cofactors) such as magnesium and/or 2,3 butanedione monoxime (BDM).

Use of these additional components may allow an optimisation of the esmolol and adenosine concentrations in the cardioplegic solution.

We show that, when 0.6 mmol/L esmolol and 0.25 mmol/l adenosine are used in combination, an improved protection is observed compared to STH in rat hearts subjected to 4 hours global ischaemia (with intermittent infusions every 20 min to mimic the protocols carried out in the operating theatre).

Here we use the same ischaemia/reperfusion procedure to examine the protection of the heart by the above esmolol+ adenosine solution, with the following modifications:
(i) effects of increased magnesium concentrations (5, 10, 15 mmol/L),
(ii) effects of increased BDM concentrations (5, 10, 20 mmol/L),
(iii) effects of combined optimal magnesium and BDM concentrations established above with changes in esmolol (0.3, 0.4, 0.5, 0.6 mmol/L) and adenosine (0.15, 0.20, 0.25 mmol/L) concentration combinations
(iv) effects of optimum solution established in (iii) compared to STH at normothermic and hypothermic ischaemia,
(v) effects of optimum solution established in (iii) when used as a blood-based solution (as is used most frequently in the clinical setting) compared to a blood-based STH at either hypothermic or 'tepid' temperatures.

With regard to the incorporation of magnesium, the following data are presented:

TABLE 3

|  | Baseline | % | 30' reperf | % | 60' reperf | % |
|---|---|---|---|---|---|---|
| Ade + Es n = 2 |  |  |  |  |  |  |
| HR | 280 |  | 290 |  | 299 |  |
| LVDP | 98 | 100 | 57 | 58.16 | 56 | 57.14 |
| EDP | 0 |  | 36 |  | 33.5 |  |
| Ad, Es, Mg 5 n = 2 |  |  |  |  |  |  |
| HR | 300 |  | 237 |  | 263 |  |
| LVDP | 101 | 100 | 49 | 48.51 | 53 | 52.48 |
| EDP | 7 |  | 72.5 |  | 66 |  |
| Ad, Es Mg10 n = 3 |  |  |  |  |  |  |
| HR | 290 |  | 267 |  | 269 |  |
| LVDP | 114.3 | 100 | 78.3 | 68.50 | 74.3 | 65.00 |
| EDP | 3 |  | 35 |  | 33.3 |  |
| Ad, Es Mg 15 n = 3 |  |  |  |  |  |  |
| HR | 310 |  | 300 |  | 304 |  |
| LVDP | 116.3 | 100 | 59.6 | 51.25 | 63 | 54.17 |
| EDP | 2.6 |  | 45 |  | 39.6 |  |

Figure 5:
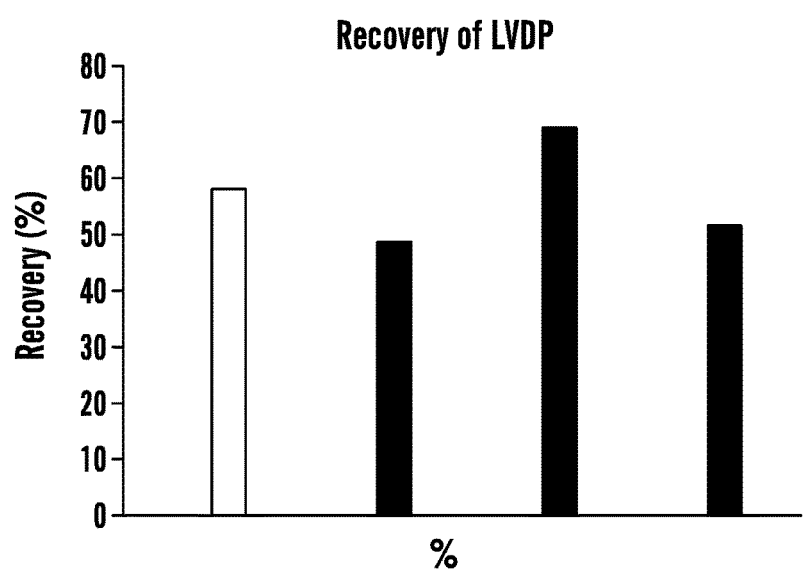
FIG. 5 shows a bar chart The invention is now described by way of example. These examples are intended to be illustrative, and are not intended to limit the appended claims.

Reference is made to FIG. 5 which shows a bar chart of the 30 minute reperfusion data for different Mg concentrations.

Thus it can be appreciated that 10 mM magnesium offers a particular advantage of enhanced recovery (LVDP after reperfusion). Thus suitably the composition of the invention comprises 10 mM magnesium.

By following this procedure for other additives and/or other Mg concentrations, the skilled worker may further optimise the concentrations of such elements of the compositions of the invention.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

We claim:
1. A method for inducing cardioplegia in a human subject, said composition comprising administering to the human subject a composition comprising.
   (i) esmolol; and
   (ii) adenosine;
   wherein the concentration of said esmolol is in the range 0.5 mM to 1.5 mM, wherein the concentration of said adenosine is in the range 0.25 mM to 1.5 mM, wherein the product of the concentration of esmolol and of adenosine is at least 0.15, wherein the product of the concentration is calculated by multiplying the concentration of esmolol and the concentration of adenosine expressed using millimolar concentration units.
2. The method according to claim 1, wherein the composition does not comprise lidocaine.
3. The method according to claim 1, wherein the concentrations of esmolol and adenosine correspond to a single point in the enclosed area on the graph of FIG. 4.

4. The method according to claim 2, wherein the concentrations of esmolol and adenosine correspond to a single point in the hatched area within the enclosed area on the graph of FIG. 4.

5. The method according to claim 1, wherein the product of the concentration of esmolol and of adenosine is at least 0.3.

6. The method according to claim 1, wherein said composition comprises a blood preparation.

7. The method according to claim 1, wherein said composition comprises a crystalloid preparation.

8. The method according to claim 1, wherein said composition comprises 0.6 mM esmolol and 0.25 mM adenosine.

9. The method according to claim 1, wherein said esmolol and adenosine are dissolved in a solvent consisting essentially of Ringer solution.

10. The method according to claim 1, further comprising 10 mM $Mg^{2+}$.

11. The method according to claim 1, wherein the composition is administered at about 22-24 degrees of Celcius.

12. The method according to claim 1, wherein the composition further comprises Ringer's solution.

13. The method according to claim 1, wherein the product of the concentration of esmolol and of adenosine is at least 0.3.

14. The method according to claim 1, wherein the composition further comprises 4-20 mM potassium (K+).

* * * * *